US00PP34916P2

(12) United States Plant Patent
Stewart et al.

(10) Patent No.: US PP34,916 P2
(45) Date of Patent: Jan. 17, 2023

(54) STRAWBERRY PLANT NAMED 'DRISSTRAWONEHUNDRED'

(50) Latin Name: ***Fragaria* x *ananassa***
Varietal Denomination: 'DrisStrawOneHundred'

(71) Applicant: Driscoll's, Inc., Watsonville, CA (US)

(72) Inventors: Philip J. Stewart, Watsonville, CA (US); Joanne F. Coss, Watsonville, CA (US); Amy M. Edmondson, Watsonville, CA (US); Iana Kostina, Watsonville, CA (US); Debora Liabeuf, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/855,329

(22) Filed: Jun. 30, 2022

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409; A01H 5/08
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr. et al.
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 Lopez
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,363 P2 9/2009 Chandler
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.
PP21,559 P2 12/2010 Ferguson et al.
PP21,762 P2 3/2011 Stewart et al.
PP22,040 P3 7/2011 Stewart et al.
PP22,218 P2 11/2011 Ferguson et al.
PP22,247 P2 11/2011 Ferguson
PP23,107 P2 10/2012 Ferguson et al.
PP23,148 P2 10/2012 Gilford et al.
PP23,377 P2 2/2013 Ferguson et al.
PP23,378 P2 2/2013 Pullen et al.
PP23,382 P2 2/2013 Ferguson et al.
PP23,383 P2 2/2013 Ferguson et al.
PP23,400 P2 2/2013 Ferguson et al.

(Continued)

*Primary Examiner* — Keith O. Robinson

(74) *Attorney, Agent, or Firm* — Morrison & Foerster LLP

(57) ABSTRACT

A new and distinct variety of strawberry plant named 'DrisStrawOneHundred', particularly selected for the whitish color and flavor of its fruit, as well as its limited mildew susceptibility, is disclosed.

7 Drawing Sheets

(56) References Cited

U.S. PATENT DOCUMENTS

| | | | |
|---|---|---|---|
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| PP30,775 | P2 | 8/2019 | Carrillo Mendoza et al. |
| PP30,789 | P2 | 8/2019 | Ferguson et al. |
| PP30,818 | P2 | 8/2019 | Pakozdi et al. |
| PP30,851 | P2 | 8/2019 | Fear et al. |
| PP30,936 | P2 | 10/2019 | Stewart et al. |
| PP31,083 | P2 | 11/2019 | Carrillo Mendoza et al. |
| PP31,233 | P2 | 12/2019 | Pakozdi et al. |
| PP31,527 | P3 | 3/2020 | Carrillo Mendoza et al. |
| PP31,655 | P2 | 4/2020 | Carrillo Mendoza et al. |
| PP31,703 | P2 | 4/2020 | Stewart et al. |
| PP31,827 | P2 | 6/2020 | Ferguson et al. |
| PP31,896 | P2 | 6/2020 | Pakozdi et al. |
| PP31,935 | P2 | 7/2020 | Pakozdi et al. |
| PP32,079 | P2 | 8/2020 | Carrillo Mendoza et al. |
| PP32,080 | P2 | 8/2020 | Ferguson et al. |
| PP32,271 | P2 | 10/2020 | Ferguson et al. |
| PP32,305 | P3 | 10/2020 | Pakozdi et al. |
| PP32,498 | P2 | 11/2020 | Mendoza et al. |
| PP32,499 | P3 | 11/2020 | Jacobs et al. |
| PP32,500 | P3 | 11/2020 | Stewart et al. |
| PP32,801 | P2 | 2/2021 | Ferguson et al. |
| PP32,814 | P2 | 2/2021 | Stewart et al. |
| PP32,824 | P2 | 2/2021 | Stewart et al. |
| PP33,070 | P2 | 5/2021 | Mendoza et al. |
| PP33,090 | P2 | 5/2021 | Mendoza et al. |
| PP33,283 | P2 | 7/2021 | Stewart et al. |
| PP33,513 | P2 | 9/2021 | Stewart et al. |
| PP33,737 | P2 | 12/2021 | Hernandez et al. |
| PP33,738 | P2 | 12/2021 | Stewart et al. |
| PP34,072 | P2 | 3/2022 | Mendoza et al. |
| PP34,212 | P2 | 5/2022 | Jacobs et al. |
| PP34,241 | P2 | 5/2022 | Pakozdi et al. |
| PP34,273 | P2 | 5/2022 | Mendoza et al. |
| PP34,274 | P2 | 5/2022 | Ferguson et al. |
| PP34,440 | P2 | 7/2022 | Nguyen et al. |
| PP34,441 | P2 | 7/2022 | Nguyen et al. |
| 2003/0079263 | P1 | 4/2003 | Gilford et al. |
| 2013/0276182 | P1 | 10/2013 | Fear et al. |

STRAWBERRY PLANT NAMED 'DRISSTRAWONEHUNDRED'

Latin name:

Botanical classification: *Fragaria* x *ananassa.*

Varietal denomination: The varietal denomination of the claimed variety of strawberry plant is 'DrisStrawOneHundred'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawOneHundred'.

Strawberry plant variety 'DrisStrawOneHundred' originated from a controlled cross between the female parent 'DrisStrawFiftySeven' (U.S. Plant Pat. No. 29,728) and the proprietary male parent '21AA176' (unpatented). Progeny plants from this cross, including 'DrisStrawOneHundred', were asexually propagated via stolons in Shasta County, Calif. in May 2014. Strawberry plant variety 'DrisStrawOneHundred' was later specifically identified and selected in Monterey County, Calif. in April 2015.

'DrisStrawOneHundred' was subsequently asexually propagated via stolons, and has undergone testing at test plots in Monterey County, Calif. for seven years (2015 to 2022). The present variety has been found to be stable and reproduce true to type through successive asexual propagations via stolons and tissue culture.

'DrisStrawOneHundred' was particularly selected for the whitish color and flavor of its fruit, as well as its limited mildew susceptibility.

DESCRIPTION OF THE DRAWINGS

This new strawberry plant is illustrated by the accompanying photographs. The colors shown are as true as can be reasonably obtained by conventional photographic procedures. Unless otherwise indicated, the photographs are of plants that are nine months old.

DETAILED BOTANICAL DESCRIPTION

Figure 1:
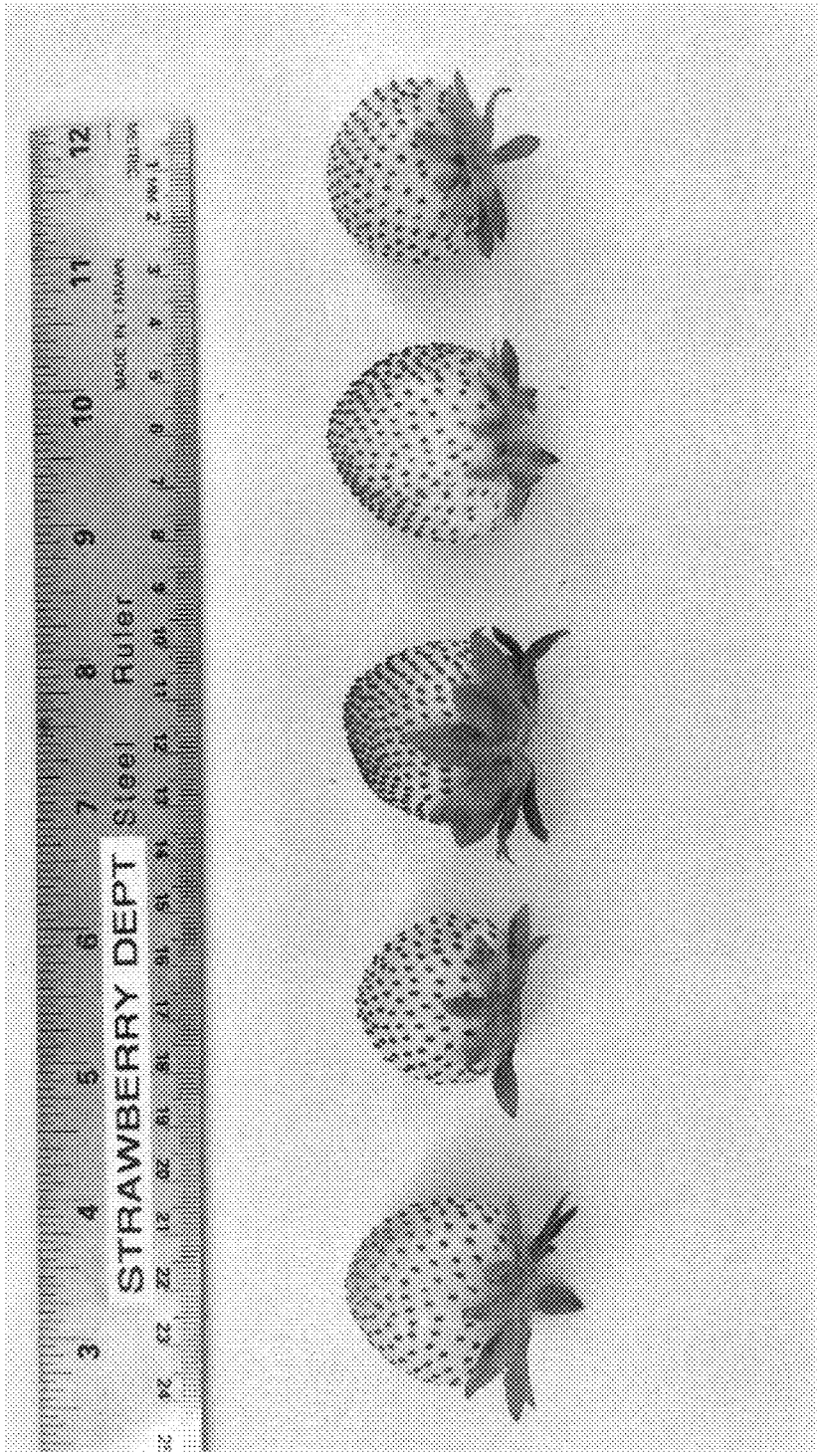
FIG. 1 illustrates whole fruit of variety 'DrisStrawOneHundred'.
Figure 2:
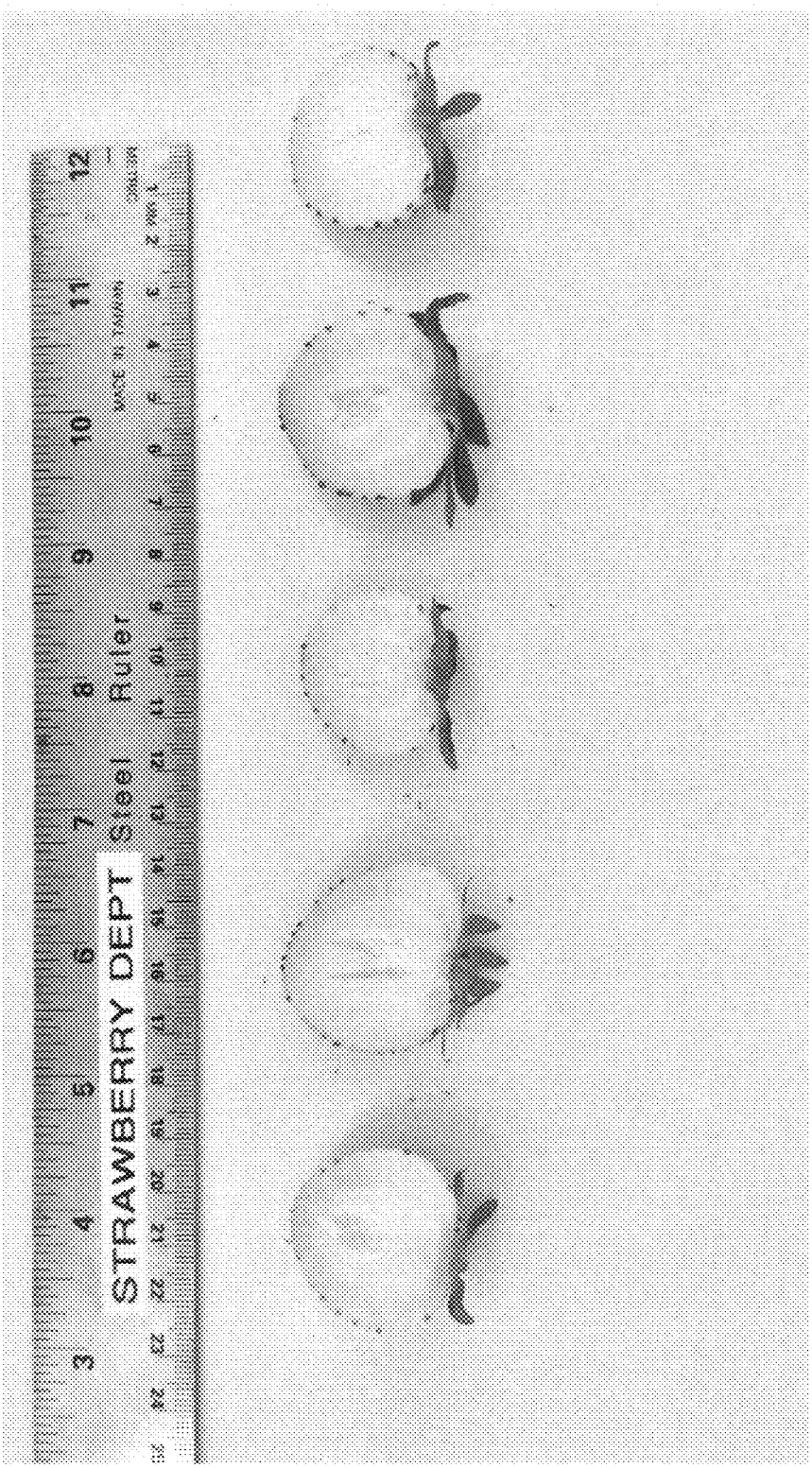
FIG. 2 illustrates longitudinal sections of fruit of variety 'DrisStrawOneHundred'.
Figure 3:
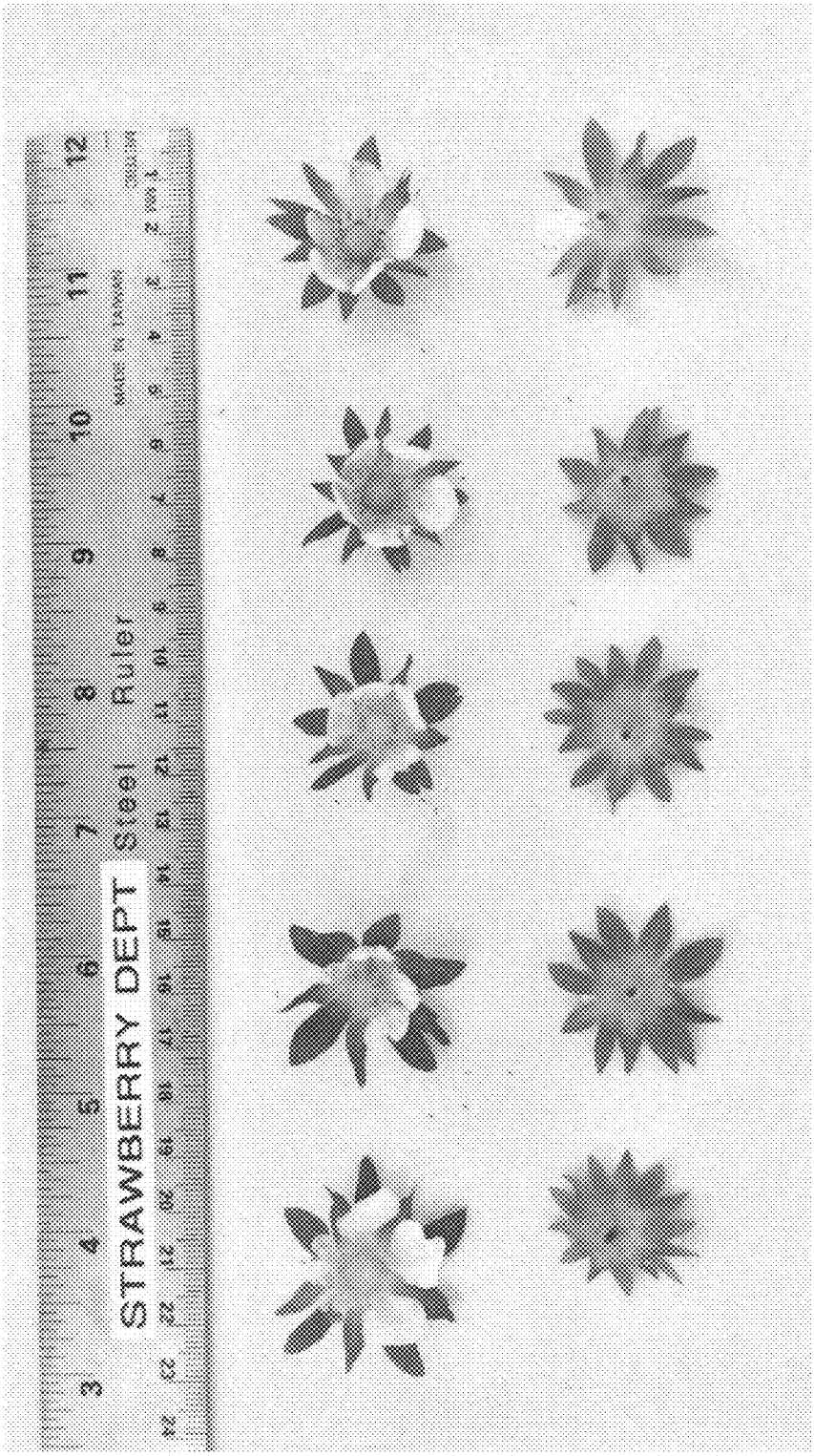
FIG. 3 illustrates the upper surface (top row) and lower surface (bottom row) of flowers of variety 'DrisStrawOneHundred'.
Figure 4:
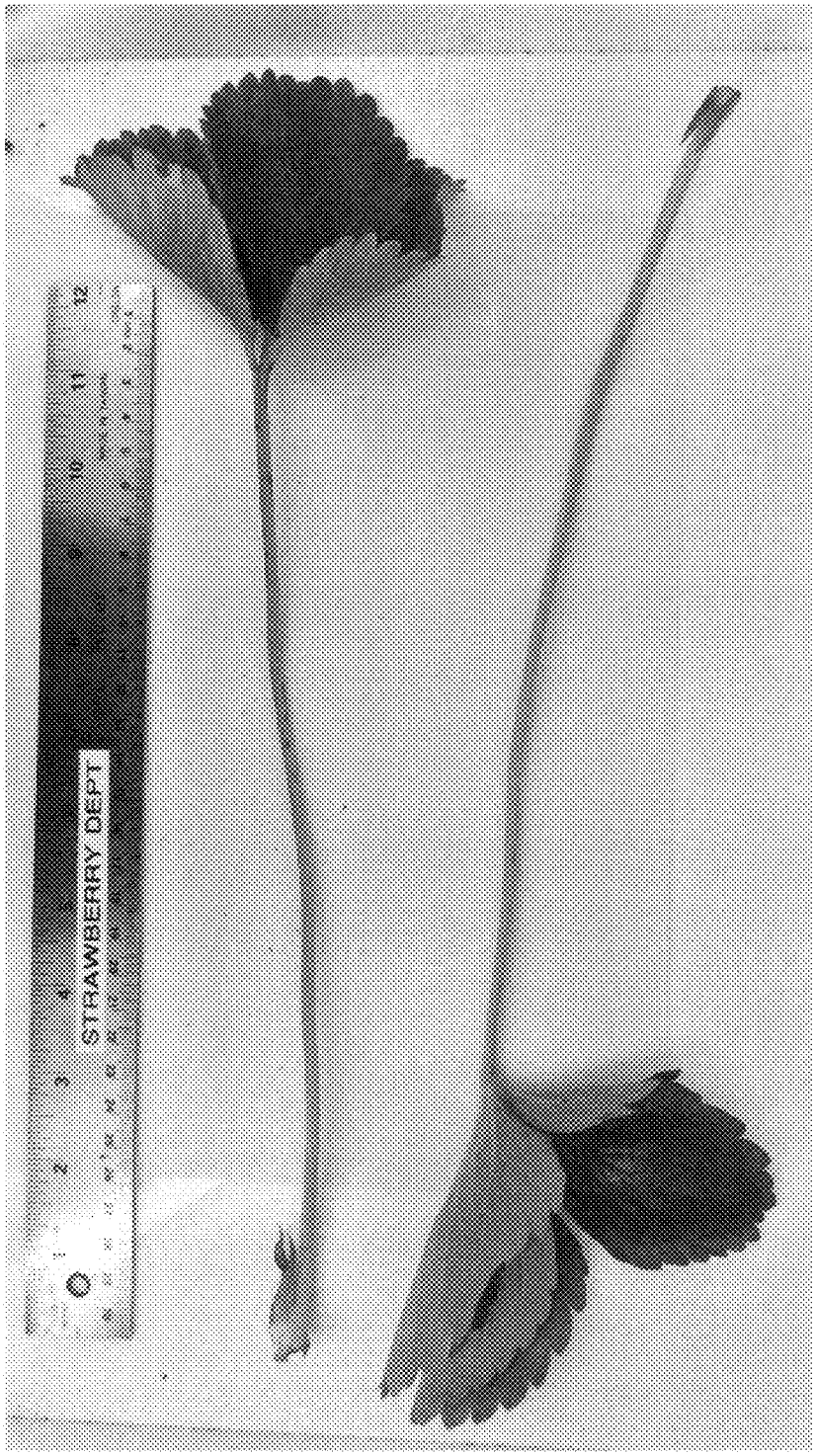
FIG. 4 illustrates the upper surface (top row) and lower surface (bottom row) of leaves of variety 'DrisStrawOneHundred'.
Figure 5:
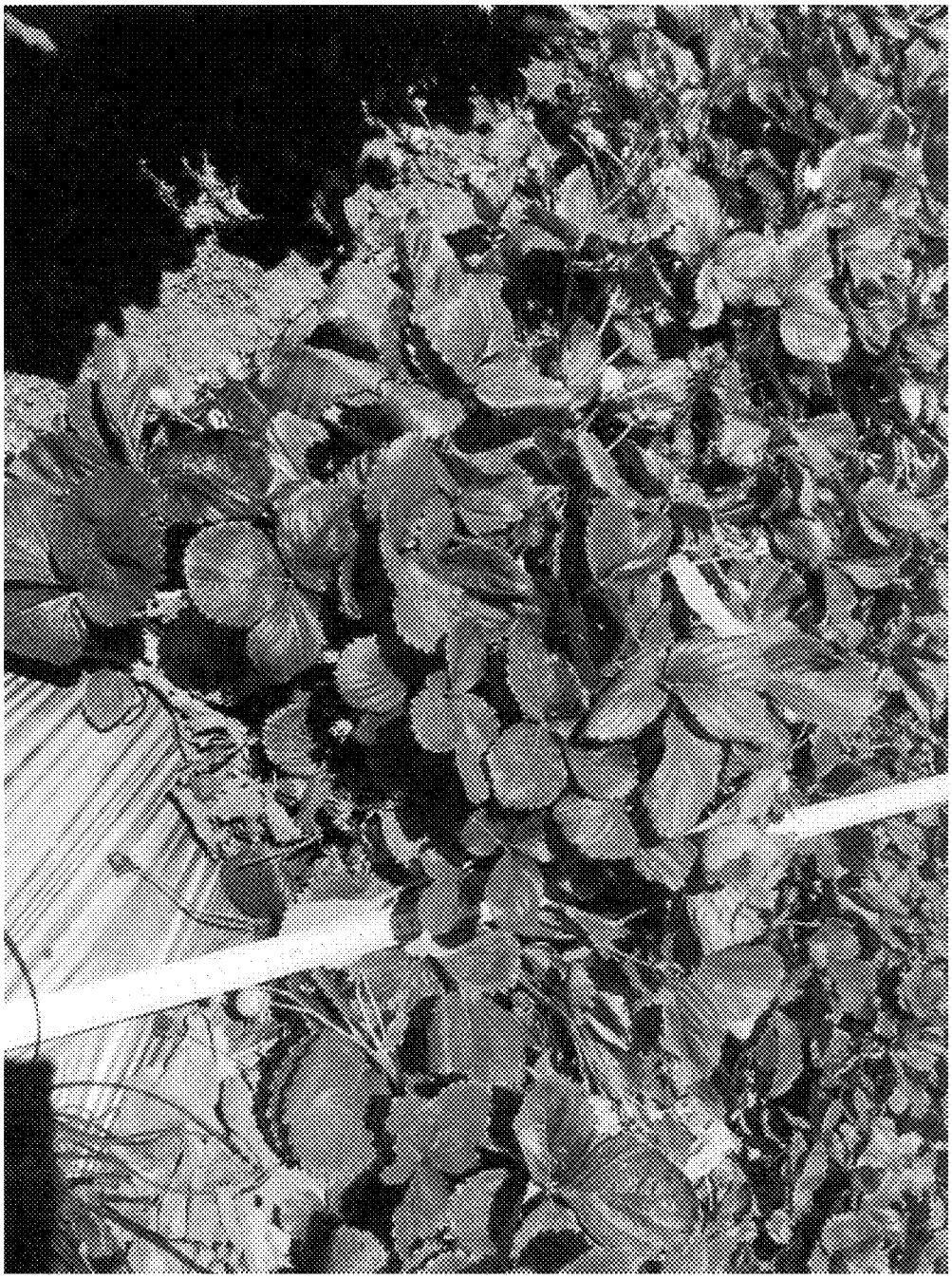
FIG. 5 illustrates whole plants of variety 'DrisStrawOneHundred'.
Figure 6:
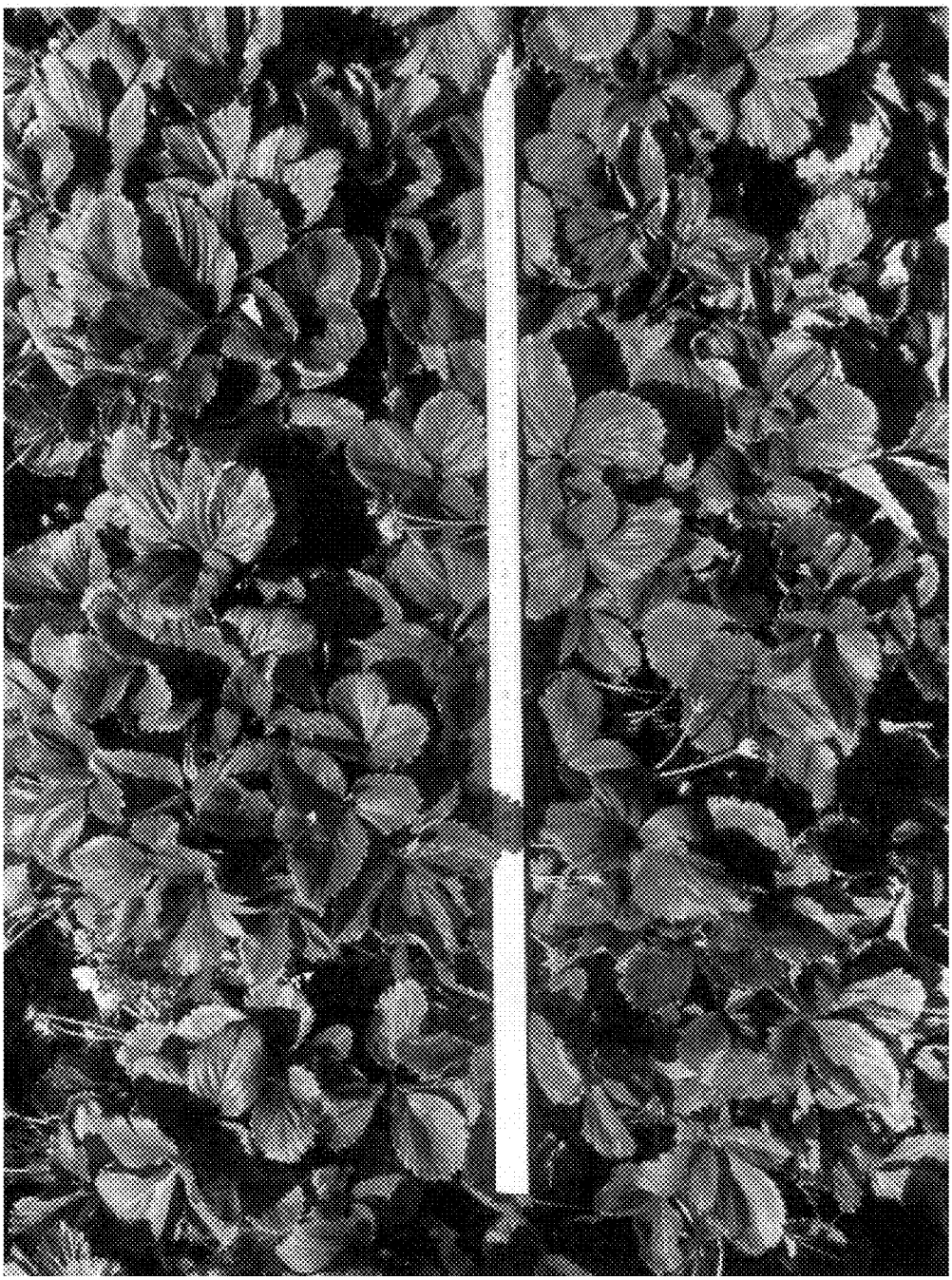
FIG. 6 illustrates an aerial view of whole plants of variety 'DrisStrawOneHundred'.
Figure 7:
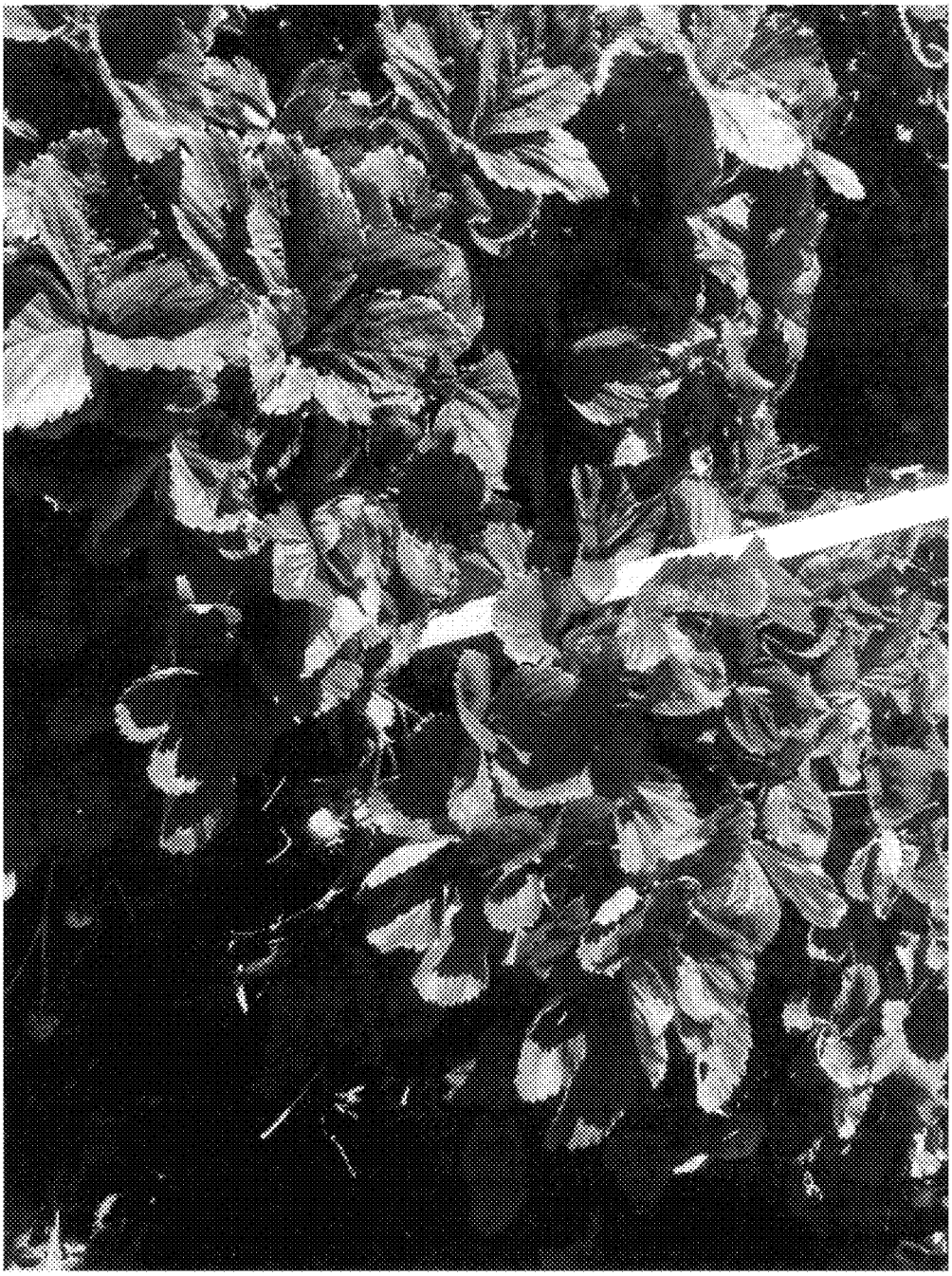
FIG. 7 illustrates another view of whole plants of variety 'DrisStrawOneHundred'.

The following detailed descriptions set forth the distinctive characteristics of 'DrisStrawOneHundred'. The data which define these characteristics is based on observations taken in Monterey County, Calif. from 2015 to 2022. This description is in accordance with UPOV terminology. Color designations, color descriptions, and other phenotypical descriptions may deviate from the stated values and descriptions depending upon variation in environmental, seasonal, climatic, and cultural conditions. 'DrisStrawOneHundred' has not been observed under all possible environmental conditions. The botanical description of 'DrisStrawOneHundred' was taken from plants that were nine months old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Species.*—*Fragaria* x *ananassa.*

*Common name.*—Strawberry.

*Denomination.*—'DrisStrawOneHundred'.

Parentage:

*Female parent.*—'DrisStrawFiftySeven' (U.S. Plant Pat. No. 29,728).

*Male parent.*—Proprietary strawberry plant '21AA176' (unpatented).

Plant:

*Height.*—33 cm.

*Diameter.*—55 cm.

*Height/width ratio.*—0.60.

*Number of crowns per plant.*—11.1.

*Growth habit.*—Semi-upright.

*Density of foliage.*—Dense.

*Vigor.*—Strong.

Stolon:

*Average number of daughter plants (per square foot).*—12.

*Diameter (at bract).*—3.9 mm.

*Overall color.*—RHS 144B (Strong yellow green).

*Anthocyanin coloration.*—Absent or very weak.

*Density of pubescence.*—Medium.

Leaf:

*Number of leaflets*.—Three only.

*Color of leaf upper surface*.—RHS 139A (Dark yellowish green).

*Blistering*.—Medium.

*Glossiness*.—Medium.

*Variegation*.—Absent.

*Terminal leaflet*.—Length: 8.6 cm. Width: 7.5 cm. Length/width ratio: 1.1. Number of teeth per terminal leaflet: 21. Shape of base: Acute. Margin: Serrate to crenate. Shape in cross section: Concave.

*Petiole*.—Length: 28.1 cm. Diameter: 3.5 mm. Attitude of hairs: Slightly outwards. Bract frequency (number present on each petiole): 0.2.

*Petiolule*.—Length: 9.0 mm. Diameter: 1.9 mm.

*Stipule*.—Length: 3.4 cm. Width: 15.0 mm. Anthocyanin coloration: Weak. Anthocyanin color: RHS 174B (Greyish reddish orange).

Inflorescence:

*Position of inflorescence in relation to foliage*.—Same level.

*Flowering interval*.—February to November.

*Pedicel*.—Attitude of hairs: Horizontal.

*Flower*.—Flower diameter (petal tip to petal tip on non-flattened flower): 20.2 mm. Arrangement of petals: Free. Size of calyx in relation to corolla: Larger. Stamen: Present.

*Petal*.—Length: 10.4 mm. Width: 9.9 mm. Length/width ratio: 1.1. Number of petals per flower: 5.3. Color of upper surface: RHS 155B (Yellowish white).

*Calyx*.—Diameter (sepal tip to sepal tip, measured on back of flower): 31.7 mm.

*Sepal*.—Length: 12.0 mm. Width: 5.1 mm. Number of sepals per flower: 10.

Fruit:

*Fruit size*.—Length: 32.7 mm. Width: 31.0 mm. Length/width ratio: 1.1.

*Fruit hollow*.—Length: 14.5 mm. Width: 5.2 mm. Length/width ratio: 2.8.

*Shape*.—Ovoid.

*Difference in shape of terminal and other fruits*.—None or very slight.

*Fruit color*.—RHS 159B (Pale orange yellow).

*Evenness of color*.—Slightly uneven.

*Glossiness*.—Medium.

*Evenness of surface*.—Even or very slightly uneven.

*Width of band without achenes*.—Narrow.

*Position of achenes*.—Level with surface.

*Position of calyx attachment*.—Level with fruit.

*Attitude of sepals*.—Outwards.

*Diameter of calyx in relation to diameter of fruit*.—Slightly larger.

*Adherence of calyx*.—Very strong.

*Firmness*.—Firm.

*Color of flesh* (*excluding core*).—RHS NN155A (Yellowish white).

*Color of core*.—RHS NN155B (White).

*Fruiting*.—Harvest interval: March to early November. Type of bearing: Partially remontant. Productivity: 59,006 kg to 73,506 kg of fruit per hectare per season from six-month-old plants when grown in Aromas, Calif.

Resistance to abiotic stress, pests, and diseases:

*Powdery mildew* (*podosphaera macularis*).—Moderately susceptible.

COMPARISON WITH PARENTAL AND REFERENCE VARIETIES

'DrisStrawOneHundred' differs from the female parent and reference variety 'DrisStrawFiftySeven' (U.S. Plant Pat. No. 29,728) in that 'DrisStrawOneHundred' has an acute terminal leaflet base, weak stipule anthocyanin coloration, free petal arrangement, and narrow width of band without achenes on fruit, whereas 'DrisStrawFiftySeven' has a rounded terminal leaflet base, medium stipule anthocyanin coloration, touching to overlapping petal arrangement, and medium width of band without achenes on fruit. Further, the pink color in the fruit of 'DrisStrawOneHundred' is more pale and the fruit is more firm as compared to the fruit of 'DrisStrawFiftySeven'.

'DrisStrawOneHundred' differs from the male parent proprietary strawberry plant '21AA176' (unpatented) in that 'DrisStrawOneHundred' has greater plant vigor and lower susceptibility to powdery mildew than '21AA176'. Further, fruit of 'DrisStrawOneHundred' is more firm with improved shelf life and lower tendency to discolor than fruit of '21AA176'.

'DrisStrawOneHundred' differs from the reference variety 'DrisStrawSixtySix' (U.S. Plant Pat. No. 31,703) in that 'DrisStrawOneHundred' has an ovoid fruit shape, whitish yellow fruit color, partially remontant type of bearing, and the number of stolons is absent or very few to few, whereas 'DrisStrawSixtySix' has a conical fruit shape, medium red fruit color, day neutral type of bearing, and medium number of stolons.

We claim:

1. A new and distinct variety of strawberry plant named 'DrisStrawOneHundred' as shown and described herein.

* * * * *